US008777922B2

(12) United States Patent
Inoue et al.

(10) Patent No.: US 8,777,922 B2
(45) Date of Patent: Jul. 15, 2014

(54) MULTI-CHAMBER CONTAINER

(75) Inventors: Fujio Inoue, Naruto (JP); Isamu Tateishi, Naruto (JP); Tatsuro Tsuruoka, Tokushima (JP); Akihito Togawa, Tokushima (JP)

(73) Assignee: Otsuka Pharmaceutical Factory, Inc. (JP)

( * ) Notice: Subject to any disclaimer, the term of this patent is extended or adjusted under 35 U.S.C. 154(b) by 1013 days.

(21) Appl. No.: 12/225,543

(22) PCT Filed: Mar. 1, 2007

(86) PCT No.: PCT/JP2007/053934

§ 371 (c)(1), (2), (4) Date: Apr. 14, 2009

(87) PCT Pub. No.: WO2007/113963

PCT Pub. Date: Oct. 11, 2007

(65) Prior Publication Data

US 2009/0209935 A1 Aug. 20, 2009

(30) Foreign Application Priority Data

Mar. 31, 2006 (JP) ................................ 2006-098135
Oct. 30, 2006 (JP) ................................ 2006-294575

(51) Int. Cl.

*A61B 19/00* (2006.01)
*A61J 1/20* (2006.01)
*B65D 1/09* (2006.01)
*B65D 81/32* (2006.01)
*A61J 1/10* (2006.01)

(52) U.S. Cl.

CPC ............... *A61J 1/2093* (2013.01); *B65D 1/095* (2013.01); *A61J 2001/2024* (2013.01); *B65D 81/3266* (2013.01); *B65D 81/3277* (2013.01); *A61J 1/10* (2013.01)

USPC ............................ 604/410; 604/403; 604/408

(58) Field of Classification Search

USPC ....................................... 604/403, 408, 4, 10

See application file for complete search history.

(56) References Cited

U.S. PATENT DOCUMENTS 4,961,495 A * 10/1990 Yoshida et al. ............... 206/219
5,209,347 A * 5/1993 Fabisiewicz et al. ......... 206/219

(Continued)

FOREIGN PATENT DOCUMENTS

EP 1161932 A2 12/2001
EP 1475067 A1 11/2004

(Continued)

OTHER PUBLICATIONS

Office Action issued Nov. 18, 2011 in connection with Philippine Patent Appl. No. 1-2008-502129.

(Continued)

*Primary Examiner* — Leslie Deak

(74) *Attorney, Agent, or Firm* — Berliner & Associates

(57) ABSTRACT

It is an object of the resent invention to provide a multi-chamber container that has a weak seal portion having an increased joining strength and being easy to be opened when in administration of medicine, and that is provided at low cost. The multi-chamber container includes a medicine accommodation chamber 1, a diluting solution chamber 3 jointed to one side of the medicine accommodation chamber 1 via a partitioning weak seal portion 2, an unoccupied chamber 5 having a port 6 and joined to an opposite side of the medicine accommodation chamber 1 via a discharging weak seal portion 4, a film member 7 attached to the medicine accommodation chamber 1 for increasing a joining strength of each of the discharging weak seal portion 2 and the discharging weak seal portion 4, the discharging weak seal portion 4 having an easy-to-open portion 8 that enables the discharging weak seal portion 4 to easily opened therethrough.

8 Claims, 5 Drawing Sheets

(56) References Cited

U.S. PATENT DOCUMENTS

| | | | | |
|---|---|---|---|---|
| 5,910,138 | A | 6/1999 | Sperko et al. | |
| 5,944,709 | A | 8/1999 | Barney et al. | |
| 6,117,123 | A * | 9/2000 | Barney et al. | 604/410 |
| 6,398,771 | B1 * | 6/2002 | Gustafsson et al. | 604/410 |
| 7,243,787 | B2 * | 7/2007 | Iwasa et al. | 206/219 |
| 7,658,279 | B2 | 2/2010 | Oka et al. | |
| 2004/0134802 | A1 | 7/2004 | Inoue | |
| 2005/0087456 | A1 * | 4/2005 | Oka et al. | 206/219 |
| 2009/0299324 | A1 * | 12/2009 | Inoue et al. | 604/410 |

FOREIGN PATENT DOCUMENTS

| | | |
|---|---|---|
| EP | 1579839 A2 | 9/2005 |
| JP | 3-85038 | 8/1991 |
| JP | 2002-136570 | 5/2002 |
| JP | 2002234101 | 8/2002 |
| JP | 2003-159310 | 6/2003 |
| JP | 2005-096869 | 4/2005 |
| JP | 2005-10046 | 11/2005 |
| TW | 384221 | 3/1989 |
| TW | 200303193 A | 9/2003 |

OTHER PUBLICATIONS

Office Action issued Mar. 16, 2012 in connection with Taiwanese Patent Appl. No. 096110032.

European Search Report issued Jul. 23, 2013 in connection with related European Patent Appl. No. 07737614.3.

* cited by examiner (a)

(b)

MULTI-CHAMBER CONTAINER

FIELD OF THE INVENTION

The present invention relates to a multi-chamber container that allows various unstable medicines (liquid medicine, powder or solid medicine), which are likely to be deteriorated with age when they are previously mixed together, to be accommodated therein separately from each other, and allows them to be used by being aseptically mixed when administering.

RELATED ART

Of medicines to be intravenously administered to patients, there are unstable medicines that may cause undesirable deterioration with age when they are previously mixed. For example, when the mixed liquid of amino-acid infusion and glucose infusion is stored, a so-called Maillard reaction occurs and the mixed liquid turns brownish. When the mixture of fat emulsion and electrolyte solution is stored, fat therein is condensed, and when the mixture of phosphoric acid-containing liquid and calcium-containing liquid is stored, calcium phosphate precipitates and hence undesirable deterioration may occur.

For those medicines, a multi-chamber container for separately accommodating unmixed components therein is frequently used. This multi-chamber container has plural chambers for accommodating medicines separately from each other, and a partitioning weak seal portion provided between the chambers, which seal can be opened by pressure applied from the outside. The multi-chamber container of this type stores medicines separated from each other via the partitioning weak seal portion until used, and allows the medicines to be aseptically mixed when administering. In recent years, a risk of causing a trouble (medical accident), such as a trouble of erroneously administering a medicine of only one chamber due to forgetting to open the partition, has started to be brought up.

In order to prevent the occurrence of the above trouble, there is proposed a medical multi-chamber container that allows medicines accommodated in the respective chambers to be administered after they have been securely mixed. For example, a medical multi-chamber container as proposed has plural accommodation chambers jointed to each other via a partitioning weak seal portion, and a discharging weak seal portion provided between at least one accommodation chamber and a discharge port, in which the discharging weak seal portion has a sealing strength (joining strength) larger than that of the partitioning weak seal portion (cf., Patent Document 1 for example). This medical multi-chamber container allows the partitioning weak seal portion to be opened before the discharging weak seal portion is opened when mixing the medicines by pressing the respective accommodation chambers, and therefore it is possible to prevent the discharging weak seal portion from being solely opened and hence prevent erroneous administration.

There is also proposed a medical multi-chamber container, in which a discharging weak seal portion has a sealing strength smaller than that of a partitioning weak seal portion (cf., Patent Document 2 for example). This medical multi-chamber container allows the partitioning weak seal portion to be opened by pressing an accommodation chamber that is located farther to the discharge port than the other chamber, thereby mixing the medicines together, and then allows the discharging weak seal portion to be opened by pressing the entire portion of the container, when in administration. Since the discharging weak seal portion has a smaller sealing strength, it has an advantage of being easily opened.

Patent Document 1: Japanese Patent Application Laid-Open No. 2002-136570
Patent Document 2: Japanese Patent Application Laid-Open No. 2003-159310

DISCLOSURE OF THE INVENTION

Problems to be Solved by the Invention

However, when the difference in sealing strength is to be set between the partitioning weak seal portion and the discharging weal seal portion, as described in the above two prior arts, complicated design conditions are necessitated to set seal width, heating time, heating temperature, applied pressure, etc, and complicated manufacturing processes are also necessitated, which poses a problem of increasing costs. For example, when a large seal width is set for improvement of the sealing strength, a problem of decreasing the volume of an accommodation chamber may be caused, and when a long heating time is set, a problem of deteriorating the productivity may be caused.

Since a weak seal portion is formed by heat bonding films together under pressure after medicines or diluting solution have been accommodated in a container, the joining strength is low and therefore there is a drawback that the weak seal portion is easy to be opened by external force. Since it is difficult to completely omit external force acting on a multi-chamber container in a transportation process after shipping or the like, and there is a fear that an external force unintentionally acts on a multi-chamber bag due to handling even after the transportation.

Therefore, there is a demand for a simple method that is capable of securely improving the joining strength of a weak seal portion after the accommodation of medicines or diluting solution, without the necessity to enlarge the seal width or elongate the heating time, so as not to have the weal seal portion opened before the administration. There is also a demand for a means of easily opening a discharging weak seal portion, taking into account a case where both the partitioning weak seal portion and the discharging weak seal portion are to have increased joining strength, since a sealed space is increased after the opening of the partitioning weak seal portion for administration.

In consideration of the above, it is an object of the present invention to provide a multi-chamber container that has a weak seal portion having an increased joining strength and being easy to be opened when in administration, and that is provided at low cost.

Means for Solving Problems (1) According to the present invention, there is provided a multi-chamber container that is characterized in that it includes a medicine accommodation chamber, a diluting solution chamber jointed to one side of the medicine accommodation chamber via a partitioning weak seal portion, an unoccupied chamber having a port and joined to an opposite side of the medicine accommodation chamber via a discharging weak seal portion, and a film member attached to the medicine accommodation chamber for increasing a joining strength of each of the partitioning weak seal portion and the discharging weak seal portion, the discharging weak seal portion having an easy-to-open portion that enables the discharging weak seal portion to be easily opened therethrough.

With the above structure, it is possible to effectively reinforce the partitioning weak seal portion and the discharging weak seal portion by a simple process, which involves attaching the film member to the medicine accommodation chamber by heat sealing, or bonding with adhesive after a medicine, diluting solution and the like have been accommodated in the chambers, and hence possible to securely improve the joining strength. Whereby, it is possible to prevent troubles such as the occurrence of unintentional rupturing of the partitioning weak seal portion and the discharging weak seal portion by an influence of external force or the like before the medicine is to be administered. When the medicine is to be administered, the partitioning weak seal portion is first opened by applying pressing force onto the diluting solution chamber, thereby mixing the medicine with the diluting solution, and then the easy-to-open portion provided in the discharging weak seal portion is opened by entirely pressing the container upon confirmation of the mixed state so that the medicine can be administered via the unoccupied chamber. Thus, the weak seal portions can be securely reinforced merely by attaching the film member to the medicine accommodation chamber. As a result, it is possible to allow for ease of designing and manufacturing, and provide the multi-chamber container at low cost. As this film member, it is possible to use a gas-barrier film or the like for protection of the medicine against oxygen or moisture, but the present invention is not intended to limit it to a specific material.

(2) The film member may have one side edge having an attaching portion that is overlapped to the partitioning weak seal portion, and an opposite side edge having an attaching portion that is overlapped to the discharging weak seal portion or located adjacent to the discharging weak seal portion on the side close to the port. With this structure, it is possible to effectively reinforce the partitioning weak seal portion and the discharging weak seal portion, and it has been confirmed from an experiment that the joining strength thereof can be securely increased.

(3) The film member may have one side edge having an attaching portion that is located adjacent to the partitioning weak seal portion on the side close to any one of the diluting solution chamber and the medicine accommodation chamber, and an opposite side edge having an attaching portion that is overlapped to the discharging weak seal portion or located adjacent to the discharging weak seal portion on the side close to the port. With this structure, it is possible to effectively reinforce the partitioning weak seal portion and the discharging weak seal portion, and it has been confirmed from an experiment that the joining strength thereof can be securely increased.

(4) The film member may be a gas-barrier film that substantially prevents permeation of gasses or moisture therethrough. With this, it is possible to effectively reinforce the partitioning weak seal portion and the discharging weak seal portion, and protect the medicine accommodated in the medicine accommodation chamber against oxygen or moisture.

(5) The easy-to-open portion may be formed into a shape projecting towards the medicine accommodation chamber. With this, the total pressure acting around a projecting end when the multi-chamber container has been pressed becomes greater than the other area of the discharging weak seal portion, so that the discharging weak seal portion is easy to be ruptured from the projecting end.

(6) The discharging weak seal portion may have the easy-to-open portion and straight portions extending substantially straight from opposite sides of the easy-to-open portion; the easy-to-open portion has an edge close to the unoccupied chamber, which edge having an apex and being convex towards the medicine accommodation chamber so as to be concave from the unoccupied chamber; and the apex of the edge close to the unoccupied chamber is located closer to the medicine accommodation chamber than edges of the straight portions close to the medicine accommodation chamber are. With this, it is possible to finish rupturing of the easy-to-open portion, which has started to be ruptured prior to the rupturing of the other portion due to the pressure intensively acting when the seal is opened, prior to the finish of the rupturing of the other portion, and hence instantaneously communicate the medicine accommodation chamber with the unoccupied chamber.

(7) The easy-to-open portion formed into a projecting shape may be provided in plural. With this, easier rupturing is ensured.

(8) The easy-to-open portion may be formed into a V-like shape with an apex angle of 20° to 150°. By setting the apex angle to these angles, it is possible to easily rupture from the top.

Advantages of the Invention

Since the multi-chamber container of the present invention has the partitioning weak seal portion and the discharging weak seal portion both reinforced by the film member attached to the medicine accommodation chamber, it is possible to prevent disadvantages such as the occurrence of unintentional rupturing of the partitioning weak seal portion and the discharging weak seal portion by an influence of external force or the like before the medicine is to be administered. When the medicine is to be administered, the partitioning weak seal portion is first opened by applying pressing force onto the diluting solution chamber, thereby mixing the medicine with the diluting solution, and then the easy-to-open portion is opened by entirely pressing the container upon confirmation of the mixed state so that the medicine can be administered. Thus, according to the multi-chamber container with the film member attached thereto, it is possible to allow for ease of designing and manufacturing, and provide the multi-chamber container at low cost.

DESCRIPTION OF THE REFERENCE NUMERALS

1: medicine accommodation chamber, 2: partitioning weak seal portion, 3: diluting solution chamber, 4: discharging weak seal portion, 5: unoccupied chamber, 6: port, 7: film member, 8: easy-to-open portion, 71, 72: attaching portions

Detailed Description of the Preferred Embodiment

Now, the description will be made for a multi-chamber container according to the first embodiment of the present invention with reference to the drawings attached hereto.

Figure 1:
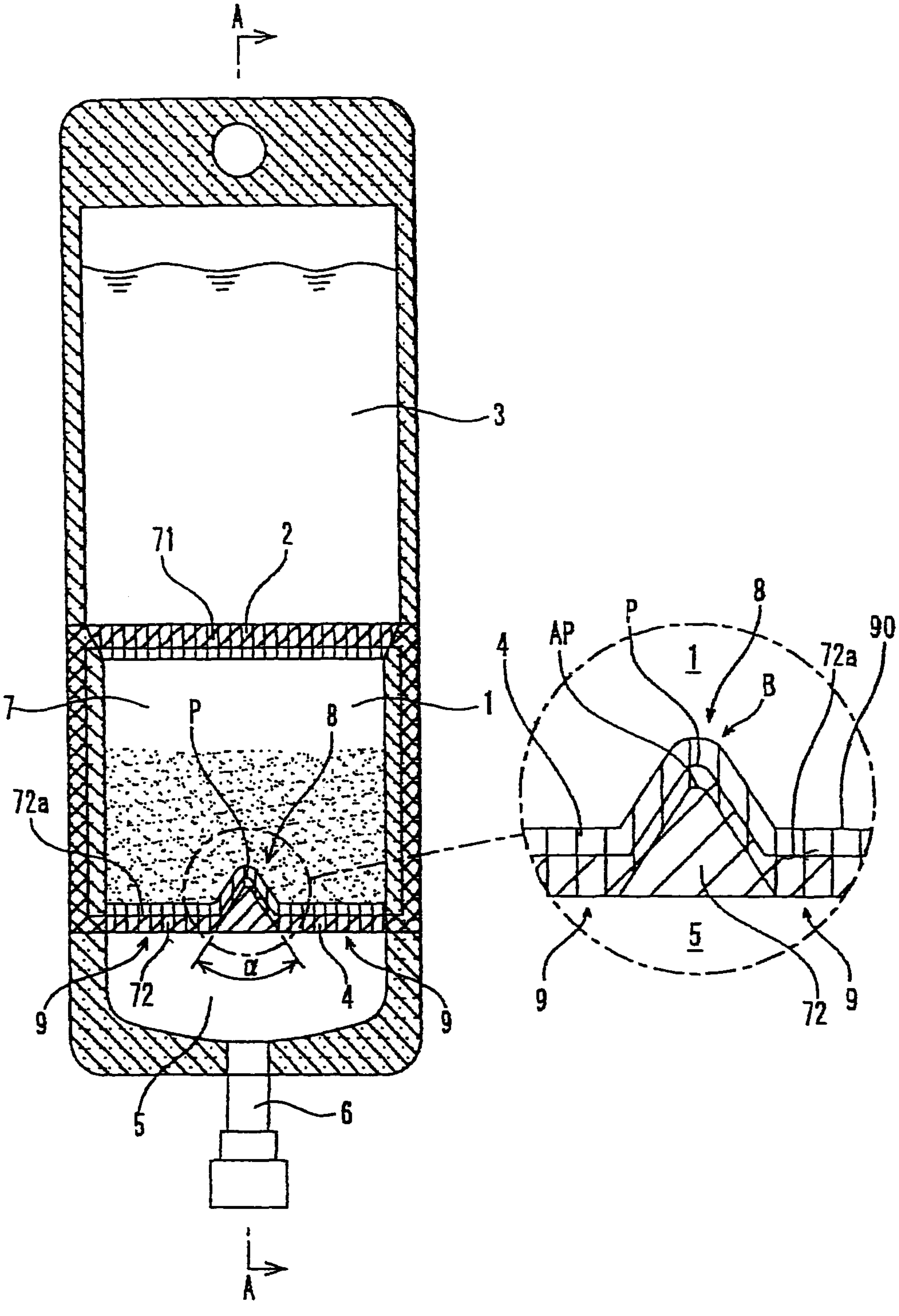
FIG. 1 is a front view of a multi-chamber container according to a first embodiment of the present invention.
Figure 2:
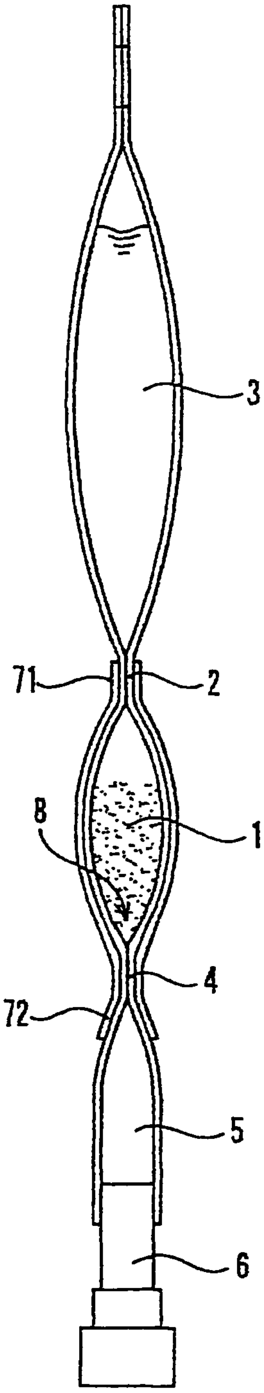
FIG. 2 is a cross sectional view of the multi-chamber container of the first embodiment.

FIG. 1 is a front view of the multi-chamber container, and FIG. 2 is a cross sectional view thereof. In these views, a reference numeral 1 represents a medicine accommodation chamber for accommodating various medicines such as antibiotic, a reference numeral 2 represents a partitioning weak seal portion provided along one side of the medicine accommodation chamber 1, a reference numeral 3 represents a diluting solution chamber, a reference numeral 4 represents a discharging weak seal portion provided along an opposite side of the medicine accommodation chamber 1, a reference numeral 5 represents an unoccupied chamber kept in antiseptic conditions, and a reference numeral 6 represents a discharging port. A film member 7 is attached on each of the front and back sides, of the medicine accommodation chamber 1 by heat sealing or bonding with adhesive or the like, in order to increase the joining strength of each of the partitioning weak seal portion 2 and the discharging weak seal portion 4.

The multi-chamber container is made up of two resin sheets (transparent resin sheets) that are overlapped to each other and sealed together throughout an outer peripheral edge thereof, thereby forming an inner space that is separated into three spaces (the medicine accommodation chamber 1, the diluting solution chamber 3 and the unoccupied chamber 5) by the partitioning weak seal portion 2 and the discharging weak seal portion 4. The multi-chamber container of this embodiment is formed into an elongated shape, has the partitioning weak seal portion 2 extending in a width direction (direction orthogonal to the lengthwise direction), thereby defining the medicine accommodation chamber 1 and the diluting solution chamber 3, and has the discharging weak seal portion 4 extending in the same direction as the partitioning weak seal portion 2, thereby defining the medicine accommodation chamber 1 and the unoccupied chamber 5. Thus, the dilution solution chamber 3, the medicine accommodation chamber 1 and the unoccupied chamber 5 are formed to be aligned in this order in the lengthwise direction from above.

The film members 7 each have a one side edge having an attaching portion 71 that is overlapped and attached to the partitioning weak seal portion 2, and an opposite side edge having an attaching portion 72 that is overlapped and attached to the discharging weak seal portion 4. Specifically, the film members 7 are respectively attached to the outer surfaces of the two transparent resin sheets that together form the medicine accommodation chamber 1, the diluting solution chamber 3 and the unoccupied chamber 5, while covering an area defining the medicine accommodation chamber 1 from the outside, and having the upper and lower attaching portions 71, 72 being respectively overlapped to the partitioning weak seal portion 2 and the discharging weak seal portion 4.

As the film members 7, it is possible to use a gas-barrier film or the like that substantially prevents permeation of gasses and moisture therethrough, but as long as the gas-barrier capability is not required, a material for them can be appropriately selected. An example of a gas-barrier film includes a gas-barrier film that has a barrier film layer made up of a laminate formed by vapor depositing silica and/or alumina on polyethylene terephthalate (PET), and an olefin resin such as polyethylene (PE) attached to the laminate.

It is possible to protect the medicine from the influence of moisture or oxygen without the necessity to use a drying agent, a deoxidant or the like by attaching these films 7 to the medicine accommodation chamber 1. When the film members 7 are formed by using a gas-barrier film, the film members 7 are respectively attached to the outer surfaces (the sealed areas of the resin sheets) of the two transparent resin sheets, which together form the medicine accommodation chamber 1, the diluting solution chamber 3 and the unoccupied chamber 5, along the lateral side edges positioned opposite to each other in the width direction of the multi-chamber container. Whereby, the film members 7, which cover the medicine accommodation chamber 1, each have an entire periphery sealed around the medicine accommodation chamber 1, so that moisture, oxygen, etc., outside the container are prevented from permeating into the inside of the chamber 1. Since the film members 7 are transparent, the inside of the medicine accommodation chamber 1 is visible from the outside, and thereby it is possible to clearly check the conditions of the accommodated medicine, and the presence or absence of insoluble foreign matters in the medicine accommodation chamber 1, when a diluting solution has been introduced into the medicine accommodation chamber 1 from the diluting solution chamber 3 and mixed with the medicine by breaking the partitioning weak seal portion 2. Thus, the occurrence of erroneous administration can be suppressed.

Since the medicine accommodation chamber 1 is covered with the transparent film members 7, it is possible to clearly detect any foreign matters or the like mixed during the manufacturing process. For example, when a label with both sides printed is attached on either side of the diluting solution chamber 3, the label can be observed from the outside through the medicine accommodation chamber 1 and the diluting solution chamber 3 even when they are folded into two along the partitioning weak seal portion 2.

Since the diluting solution chamber 3 is joined to the medicine accommodation chamber 1 via the partitioning weak seal portion 2, the partitioning weak seal portion 2 can be opened by pressing the multi-chamber container around the diluting solution chamber 3 and thus the medicine is necessarily introduced into the unoccupied chamber 5 after it has been diluted with the diluting solution. Therefore, the medicine diluted via the unoccupied chamber 5 can be administered and the occurrence of erroneous administration can be prevented. Also, since the medicine accommodation chamber 1 covered with the gas-barrier film member 7 is joined via the discharging weak seal portion 4 to the unoccupied chamber 5 with the port 6 provided therein, the port 6 and its peripheral portion are not required to have a barrier property and therefore the material cost can be reduced. In addition, since a processed aluminum film is not used unlike the conventional container, it is possible to provide a multi-chamber container at a low price, has an improved property relative to the environment, and is easy to be disposed.

Figure 3:
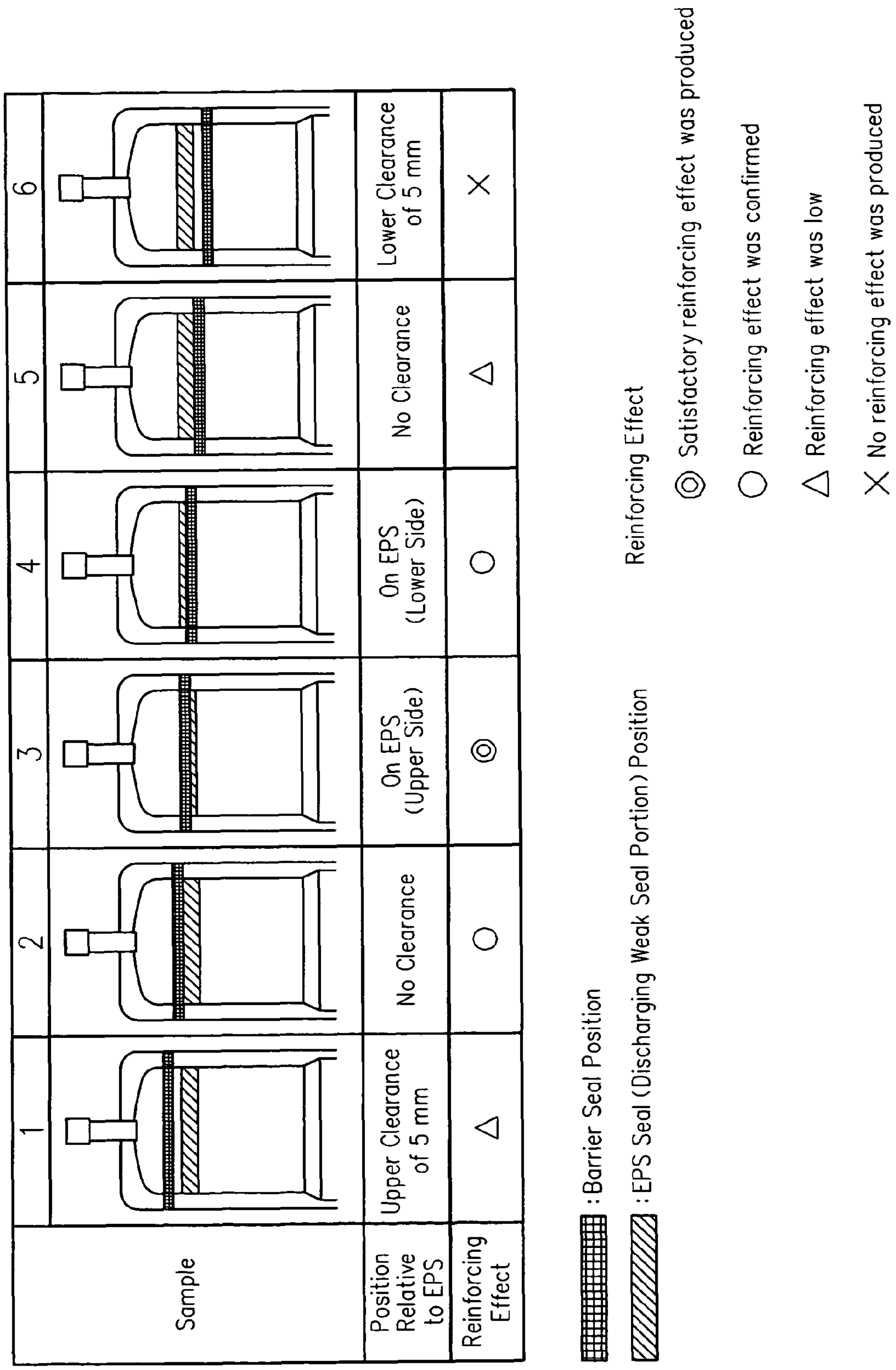
FIG. 3 illustrates the result of an experiment for confirming the effect of reinforcing weak seal portions by a film member of the first embodiment.

As described above, it is possible to effectively reinforce the partitioning weak seal portion 2 and the discharging weak seal portion 4 by overlapping the attaching portions 71, 72 of each of the film members 7, which are to be attached to the medicine accommodation chamber 1, respectively to the partitioning weak seal portion 2 and the discharging weak seal portion 4, and hence securely increase their joining strengths. Whereby, it is possible to prevent disadvantages such as the occurrence of unintentional rupturing of the partitioning weak seal portion 2 and the discharging weak seal portion 4 by an influence of external force or the like before the medicine is to be administered. The reinforcing effect by the attaching (heat sealing) of the film members 7 have been confirmed by an experiment. The result of the experiment is shown in FIG. 3.

According to the result of the experiment, in a case where the attaching portion (which is represented as the position of a barrier seal in the experiment) 72 of each of the film members 7 has been overlapped to the discharging weak seal portion (which is represented as an EPS seal portion in the experiment) 4 along the discharging side thereof, as illustrated in Sample 3, it has been confirmed that the discharging weak seal portion 72 was not easy to be opened by pressing the entire multi-chamber container after opening the partitioning weak seal portion 2, and thus a satisfactory reinforcing effect was produced. In this experiment, an easy-to-open portion 8 is not formed in the discharging weak seal portion 4, and only the reinforcing effect has been confirmed. In this embodiment, although the partitioning weak seal portion 2, to which the other attaching portion 71 of the film member 7 is attached, has also an increased joining strength, it could be promptly opened by pressing the diluting solution chamber 3. This is because a large inner pressure can be applied to the partitioning weak seal portion 2 due to the small volume of the sealed space, and therefore no trouble was experienced in opening action. The other attaching portion 71 of each of the film members 7 can also have an increased joining strength even when it is disposed on the diluting solution chamber 3 or the medicine accommodation chamber 1 adjoining the partitioning weak seal portion 2 without clearance therebetween.

For the other Samples 2 and 4, although not equivalent to Sample 3, a substantial reinforcing effect has been confirmed. Sample 2 has the attaching portion 72 disposed on the discharging side of the container adjoining the discharging weak seal portion 4 without clearance therebetween, and Sample 4 has the attaching portion 72 overlapped to the discharging weak seal portion 4 close to the medicine accommodation chamber 1. For Sample 1 having the attaching portion 72 disposed on the discharging side of the container adjacent to the discharging weak seal portion 4 with a clearance of 5 mm therebetween, and Sample 5 having the attaching portion 72 disposed on the medicine accommodation chamber 1 adjoining the discharging weak seal portion 4, a reinforcing effect was low. For Sample 6 having the attaching portion 72 disposed on the medicine accommodation chamber 1 adjacent to the discharging weak seal portion 4 with a clearance of 5 mm therebetween, little reinforcing effect was produced so that the seal was easily opened. From these results, it could be confirmed that Samples 2, 3 and 4 can be employed.

On the premise that along with the partitioning weak seal portion 2, the discharging weak seal portion 4 is reinforced, the easy-to-open portion 8 for facilitating the opening of the discharging weak seal portion 4 is provided in the discharging weak seal portion 4 in this embodiment, as illustrated in FIG. 1. Specifically, the multi-chamber container of this embodiment has the easy-to-open portion 8 for facilitating the opening of the discharging weak seal portion 4, on the premise that the reinforced discharging weak seal portion 4 is to be opened after the partitioning weak seal portion 2 has been opened, under which an inner pressure by pressing the multi-chamber container is not easy to act.

Specifically, the discharging weak seal portion 4 of this embodiment has the easy-to-open portion 8 formed into a shape projecting towards the medicine accommodation chamber 1, and straight portions 9, 9 that uninterruptedly extend substantially straight from the opposite sides of the easy-to-open portion 8. In the multi-chamber container illustrated in FIGS. 1 and 2, the attaching portion 72 of the opposite side edge of each of the film members 7 is disposed along the discharging weak seal portion 4, in which the attaching portion 72 is partially overlapped to the discharging weak seal portion 4 (the easy-to-open portion and the straight portions 9, 9) on the side close to the unoccupied chamber.

The easy-to-open portion 8 of this embodiment is formed into a V-like projection having an apex P located close to the medicine accommodation chamber 1. Specifically, the easy-to-open portion 8 has an edge close to the unoccupied chamber 5, which edge having an apex AP and being convex towards the medicine accommodation chamber 1 so as to be concave from the unoccupied chamber 5. When the easy-to-open portion 8 is formed into a projecting body having a V-like shape (chevron shape), an angle $\alpha$ of the apex of a projecting edge B is preferably from 20° to 150°.

The easy-to-open portion 8 projecting towards the medicine accommodation chamber 1 is formed to have the apex P located inward of an inner horizontal edge **72*a* (cf. FIG. 1) (located close to the medicine accommodation chamber 1) of the attaching portion 72 of each of the film members 7 located close to the medicine accommodation chamber 1. More preferably, the easy-to-open portion 8 has the apex AP of the edge close to the unoccupied chamber 5, which apex being located inward of an edge 90 of the straight portions 9, 9 close to the medicine accommodation chamber 1. The location of the apex P (AP) is essential to facilitate the opening of the discharging weak seal portion 4**.

Figure 4:
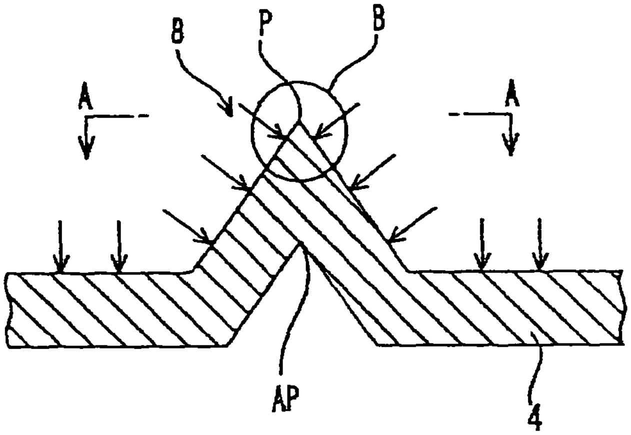
FIG. 4(*a*) is an enlarged explanatory view of an easy-to-open portion according to the first embodiment, and FIG. 4(*b*) is a cross sectional view as viewed from the allows A-A in FIG. 4(*a*).
Figure 4:
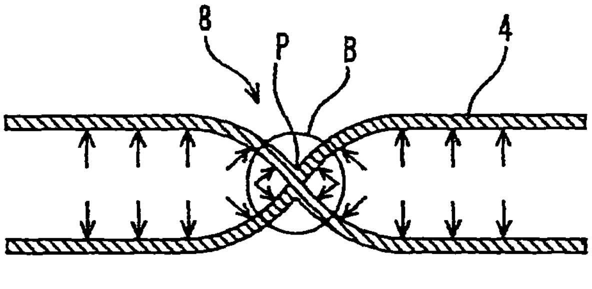

For the easy-to-open portion 8, as illustrated in FIGS. 4(*a*) and 4(*b*), when the multi-chamber container is pressed, pressure acts in the direction represented by arrows, and the total pressure acting around the outside of a projecting end B (around the edge close to the medicine accommodation chamber 1) becomes greater than the other area of the discharging weak seal portion, so that the discharging weak seal portion is easy to be ruptured from the outer periphery of the projecting end B. Specifically, even after the volume to be pressed is increased, the easy-to-open portion 8 is ruptured and hence opened from the outside of the projecting end B more instantaneously than the other portions (the straight portions 9, 9) even by a small pressing force, so that the discharging weak seal portion 4 can be easily and entirely opened by the opening of the easy-to-open portion 8.

According to the thus structured multi-chamber container, the increased joining strength of each of the partitioning weak seal portion 2 and the discharging weak seal portion 4 is maintained until the time at which the medicine is administered, it is possible to prevent troubles such as unintentional opening due to the influence of an external force. When the medicine is to be administered, the partitioning weak seal portion 2 is first opened by applying pressing force to the diluting solution chamber 3, thereby mixing the medicine with the diluting solution, and upon confirmation of mixed conditions, the multi-chamber container is entirely pressed, thereby opening the easy-to-open portion 8. Thus, the medicine can be administered. Since the multi-chamber container with the film members 7 attached to the medicine accommodation chamber 1 can be easily designed and manufactured, it can be provided at low cost.

Now, the description will be made for the multi-chamber container of the second embodiment of the present invention. The multi-chamber container of this embodiment is the same as that of the first embodiment except that seal around the easy-to-open portion (attaching portion to which a gas-barrier film is attached) has a different shape, and therefore elements identical or corresponding to those of the first embodiment are allocated the same names and codes to omit the description thereof, while the easy-to-open portion 8 and its periphery (the discharging weak seal portion 4, the easy-to-open portion 8 and the attaching portion 72 of each film member 7) will be mainly described.

Figure 5:
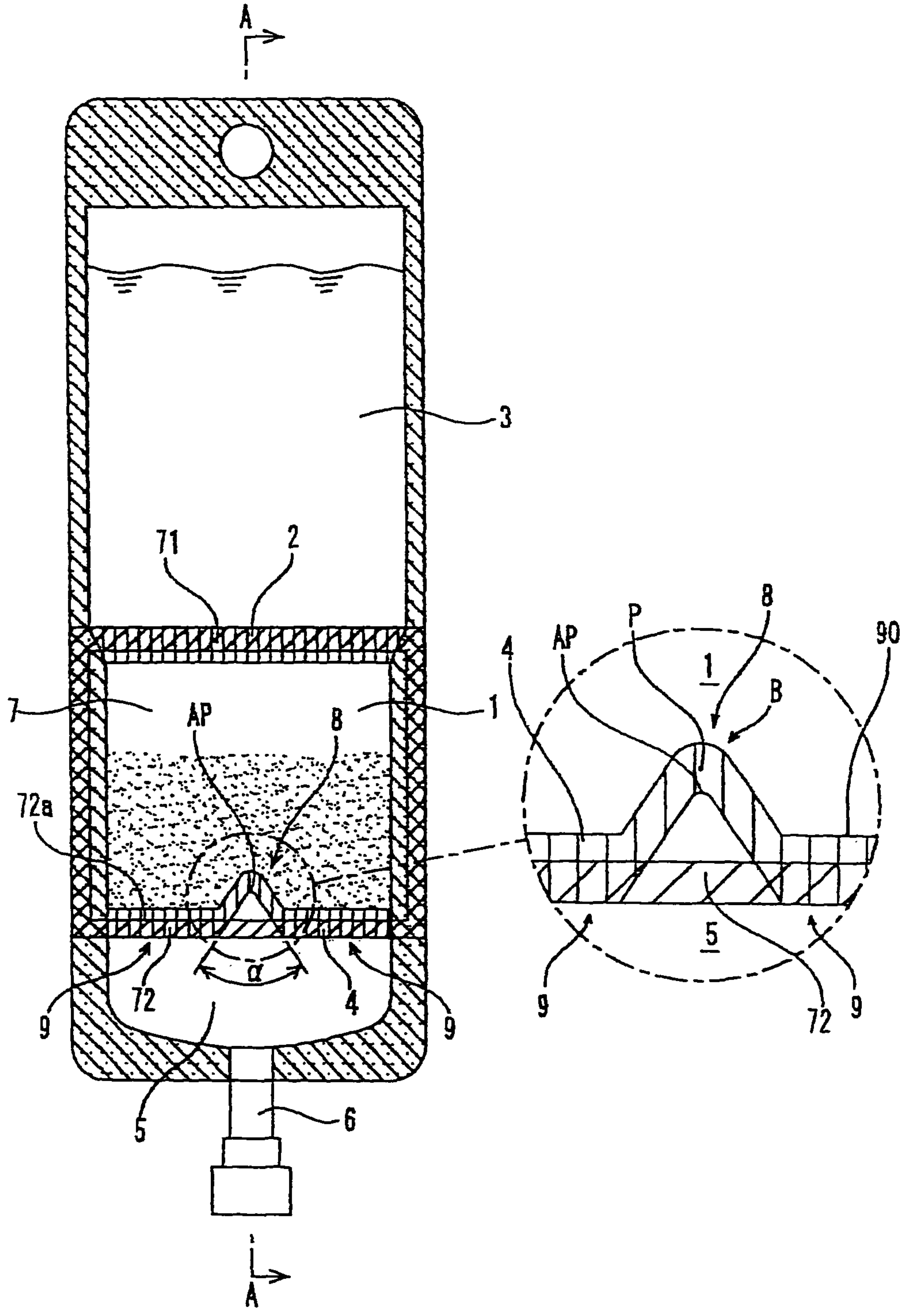
FIG. 5 is a front view of a multi-chamber container according to a second embodiment of the present invention.

As illustrated in FIG. 5, the discharging weak seal portion 4 of the multi-chamber container of this embodiment is formed to extend in the width direction of the multi-chamber container (in the direction orthogonal to an aligning direction, in which the medicine accommodation chamber 1, the diluting solution chamber 3 and the unoccupied chamber 5 are aligned), and a middle portion of the discharging weak seal portion 4 is formed into a projection towards the medicine accommodation chamber 1 to form the easy-to-open portion 8. Specifically, the discharging weak seal portion 4 has the easy-to-open portion 8, and the straight portions 9, 9 that uninterruptedly extend substantially straight from the opposite sides of the easy-to-open portion 8.

The easy-to-open portion 8 is formed into a V-like projection having the apex P located close to the medicine accommodation chamber 1 in the same manner as the first embodiment. Specifically, the easy-to-open portion 8 is formed by a bending area (V-shaped area) projecting towards the medicine accommodation chamber 1. The easy-to-open portion 8 has an edge close to the unoccupied chamber 5, which edge having the apex AP and being convex towards the medicine accommodation chamber 1 so as to be concave from the unoccupied chamber 5, in which the apex AP of the edge close to the unoccupied chamber 5 is located closer to the medicine accommodation chamber 1 than the edges of the straight portions 9, 9 close to the medicine accommodation chamber 1 are.

Contrarily to this, the attaching portion 72 of the opposite side edge (closer to the unoccupied chamber 5) of each film member 7 of this embodiment has a strip shaped area that extends substantially throughout the width of the multi-chamber container and has a substantially constant width in an aligning direction, in which the medicine accommodation chamber 1, the diluting solution chamber 3 and the unoccupied chamber 5 are aligned, and that is overlapped to the discharging weak seal portion 4 on the side close to the unoccupied chamber 5 (discharging side). That is, the attaching portion 72 of the opposite side edge of each film member 7 is attached to the discharging weak seal portion 4 substantially throughout the width of the multi-chamber container, while being partially overlapped only to the straight portions 9, 9 of the discharging weak seal portion 4 on the side close to the unoccupied chamber 5. Therefore, the multi-chamber container of this embodiment has an area surrounded by the attaching portion 72 of the film member 7 and the easy-to-open portion 8, which area being not sealed and having the film member 7 being not attached thereto.

The easy-to-open portion 8 of this embodiment is, as described above, formed by a bending area projecting towards the medicine accommodation chamber 1, so that the apex AP is also formed in the edge close to the unoccupied chamber 5. The easy-to-open portion 8 of this embodiment is formed so that the apex AP of the edge close to the unoccupied chamber 5 is located closer to the medicine accommodation chamber 1 than the edge of the discharging weak seal portion 4 (the edges of the straight portions 9, 9) close to the medicine accommodation chamber 1 is.

In the same manner as the first embodiment, the thus structured multi-chamber container has the easy-to-open portion 8 projecting towards the medicine accommodation chamber 1, so that a pressure caused by pressing the multi-chamber container intensively acts on the easy-to-open portion 8. As a result, the easy-to-open portion 8 first starts being ruptured. Since the easy-to-open portion 8 of the multi-chamber container of this embodiment has the apex AP of the edge close to the unoccupied chamber 5 being located closer to the medicine accommodation chamber 1 than the edge of the discharging weak seal portion 4 (the edges of the straight portions 9, 9) close to the medicine accommodation chamber 1 is, the easy-to-open portion 8, which has first started being ruptured, is opened prior to the rupturing of the other portions (straight portions). Whereby, as described above, even if the joining strength is reinforced by attaching the film members 7, the discharging weak seal portion 4 is entirely and easily opened, and more specifically the medicine accommodation chamber 1 is communicated with the unoccupied chamber 5, due to the rupturing (or opening) of the easy-to-open portion 8 at the time of opening (at the time of pressing the multi-chamber container).

As described above, the multi-chamber container of this embodiment can also produce the same functions and advantages as those of the first embodiment. That is, in the multi-chamber container of this embodiment, the partitioning weak seal portion 2 and the discharging weak seal portion 4 each have an increased joining strength, and therefore it is possible to prevent troubles such as the occurrence. of unintentional opening by an influence of external force before the medicine is to be administered. On the other hand, when the medicine is to be administered, the medicine can be diluted with the diluting solution by opening the partitioning weak seal portion 2 by pressing the multi-chamber container (from the side of the diluting solution chamber 3). Although an inner space (sealed space) is increased as a result of the communication of the medicine accommodation chamber 1 and the diluting solution chamber 3 and hence an inner pressure by the pressing onto the multi-chamber container is lowered, it is possible to securely and easily open the discharging weak seal portion 4 by providing the easy-to-open portion 8, and administer the diluted medicine. Thus, the multi-chamber container having the film members 7 attached to the medicine accommodation chamber 1 can be easily designed and manufactured, so that it can be provided at low cost.

The present invention is not necessarily limited to any one of the above embodiments, and can be freely subjected to design changing, modification or the like according to needs and circumstances, within the scope of the present invention.

For example, only a single film member 7 may be attached to a single side of the multi-chamber container, as long as it can provide a satisfactory reinforcing effect and a gas-barrier property is not required. When the film members are to be attached by heat sealing, a material having a heat sealing property may be selected as a film material, and also a film member having no heat sealing property may be attached with adhesive.

In any of the above embodiments, there is provided the easy-to-open portion 8 formed by a bending area (V-shaped area), but the easy-to-open portion 8 is not necessarily limited to this form. For example, the easy-to-open portion 8 may be formed by a semi-circular area or semi-elliptic area projecting towards the medicine accommodation chamber 1. That is, the easy-to-open portion 8 may be formed to have an edge close to the unoccupied chamber 5 having the apex AP and having a semi-rounded shape or semi-elliptic shape so as to be concave from the unoccupied chamber 5, and the apex AP of the semi-rounded or semi-elliptic edge is located closer to the medicine accommodation chamber 1 than the edges of the straight portions 9, 9 close to the medicine accommodation chamber 1 are.

In this case, too, the apex AP is formed in the edge of the easy-to-open portion 8 on the side close to the unoccupied chamber 5, and the apex AP is located closer to the medicine accommodation chamber 1 than the edge 90 of the discharging weak seal portion 4 (the straight portions 9, 9 extending straight from the opposite sides of the easy-to-open portion 8) close to the medicine accommodation chamber 1 is. Therefore, even if the attaching portion 72 of each film member 7 is attached to be overlapped to the discharging weak seal portion 4 so as to increase the joining strength, the discharging weak seal portion 4 can be easily and securely opened when it is to be opened.

Furthermore, in any of the above embodiments, the easy-to-open portion 8 is provided at a single place of the discharging weak seal portion 4, but it may be provided at plural places of the discharging weak seal portion 4. Specifically, plural easy-to-open portions 8 are respectively provided at plural places and these easy-to-open portions 8 are successively aligned on the straight portions 9 . . . respectively extending from the opposite sides of each of the easy-to-open portions 8. With this arrangement, a larger number of places through which the sealed portion is opened easier than the straight portions 9, 9 are provided, so that the discharging weak seal portion 4 can be more easily opened. In this case, too, it is a matter of course that the attaching portion of each film member 7 is attached closer to or onto the straight portions 9, . . .

In any of the above embodiments, the easy-to-open portion 8 is formed into a chevron shape (V-like shape) projecting towards the medicine accommodation chamber 1, but may be formed to have an angular (square, rectangular or trapezoidal) appearance projecting towards the medicine accommodation chamber 1, as shown from the front view, and to have the edge close to the unoccupied chamber 5 formed to correspond to the edge close to the medicine accommodation chamber 1 so as to be concave from the unoccupied chamber 5 in an angular (square, rectangular or trapezoidal) appearance as shown from the front view. Specifically, the easy-to-open portion 8 is formed into a shape having two or more angular portions along the opposite edges respectively close to the medicine accommodation chamber 1 and the unoccupied chamber 5, while projecting towards the medicine accommodation chamber 1 and being concave from the unoccupied chamber 5. With this arrangement, the easy-to-open portion 8 is ruptured and hence opened from the angular portions or their peripheries, of the edges. For enabling the easy-to-open portion 8 to be more easily opened, the easy-to-open portion 8 has a shape being concave from the unoccupied chamber 5, more preferably has a shape having the edge close to the unoccupied chamber 5 with the apex AP located therein, and being concave from the unoccupied chamber 5, while having the apex AP of the edge close to the unoccupied chamber 5 being located closer to the medicine accommodation chamber 1 than the edge 90 of the straight portion 9 close to the medicine accommodation chamber 1 is.

The invention claimed is:

1. A multi-chamber container comprising a medicine accommodation chamber, a diluting solution chamber jointed to one side of the medicine accommodation chamber via a partitioning weak seal portion, an unoccupied chamber having a port and joined to an opposite side of the medicine accommodation chamber via a discharging weak seal portion, and a film member attached to the medicine accommodation chamber for increasing a joining strength of the discharging weak seal portion, the discharging weak seal portion having an easy-to-open portion that enables the discharging weak seal portion to be easily opened therethrough and straight portions extending substantially straight from opposite sides of the easy-to-open portion; wherein, the easy-to-open portion has an edge close to the unoccupied chamber, which edge having an apex and being convex towards the medicine accommodation chamber so as to be concave from the unoccupied chamber; and the apex of the edge close to the unoccupied chamber is located closer to the medicine accommodation chamber than edges of the straight portions close to the medicine accommodation chamber are;

the film member has one side edge having an attaching portion that is attached in overlapping relationship to the partitioning weak seal portion, and an opposite side edge of the film member having an attaching portion that is disposed along the discharging weak seal portion, in which the attaching portion is attached in partially overlapping relationship to the straight portions on the side close to the unoccupied chamber.

2. The multi-chamber container according to claim 1, wherein the film member is a gas-barrier film that substantially prevents permeation of gasses or moisture therethrough.

3. The multi-chamber container according to claim 1, wherein the easy-to-open portion is formed into a shape projecting towards the medicine accommodation chamber.

4. The multi-chamber container according to claim 1, wherein the easy-to-open portion is formed into a V-like shape with an apex angle of 20° to 150°.

5. A multi-chamber container comprising a medicine accommodation chamber, a diluting solution chamber jointed to one side of the medicine accommodation chamber via a partitioning weak seal portion, an unoccupied chamber having a port and joined to an opposite side of the medicine accommodation chamber via a discharging weak seal portion, and a film member attached to the medicine accommodation chamber for increasing a joining strength of the discharging weak seal portion, the discharging weak seal portion having an easy-to-open portion that enables the discharging weak seal portion to be easily opened therethrough and straight portions extending substantially straight from opposite sides of the easy-to-open portion; wherein, the easy-to-open portion has an edge close to the unoccupied chamber, which edge having an apex and being convex towards the medicine accommodation chamber so as to be concave from the unoccupied chamber; and the apex of the edge close to the unoccupied chamber is located closer to the medicine accommodation chamber than edges of the straight portions close to the medicine accommodation chamber are;

the film member has one side edge having an attaching portion that is located adjacent to and attached to the partitioning weak seal portion on the side close to any one of the diluting solution chamber and the medicine accommodation chamber, and an opposite side edge of the film member having an attaching portion that is disposed along the discharging weak seal portion, in which the attaching portion is attached in partially overlapping relationship to the straight portions on the side close to the unoccupied chamber.

6. The multi-chamber container according to claim 5, wherein the film member is a gas-barrier film that substantially prevents permeation of gasses or moisture therethrough.

7. The multi-chamber container according to claim 5, wherein the easy-to-open portion is formed into a shape projecting towards the medicine accommodation chamber.

8. The multi-chamber container according to claim 5, wherein the easy-to-open portion is formed into a V-like shape with an apex angle of 20° to 150°.

* * * * *